United States Patent [19]

Cribier et al.

[11] Patent Number: 4,777,951
[45] Date of Patent: Oct. 18, 1988

[54] PROCEDURE AND CATHETER INSTRUMENT FOR TREATING PATIENTS FOR AORTIC STENOSIS

[75] Inventors: Alain Cribier, Maromme; Brice Letac, Rouen, both of France; John P. Ariola, Jr., East Providence, R.I.

[73] Assignee: Mansfield Scientific, Inc., Mansfield, Mass.

[21] Appl. No.: 909,907

[22] Filed: Sep. 19, 1986

[51] Int. Cl.$^4$ .............................................. A61M 25/00
[52] U.S. Cl. .................................... 128/344; 128/672; 128/748; 604/96
[58] Field of Search ............... 128/672, 673, 748, 344, 128/348.1; 604/96-103

[56] References Cited

U.S. PATENT DOCUMENTS

| | | | |
|---|---|---|---|
| 3,348,548 | 10/1967 | Chardack | 128/418 |
| 3,419,010 | 1/1966 | Williamson | 128/350 |
| 3,729,008 | 4/1973 | Berkovits | 128/418 |
| 3,890,977 | 6/1975 | Wilson | 128/418 |
| 4,154,247 | 5/1979 | O'Neill | 128/419 |
| 4,357,947 | 11/1982 | Litteford | 128/786 |
| 4,394,866 | 7/1983 | Hughes | 128/785 |
| 4,413,989 | 11/1983 | Schjeldahl et al. | 604/96 |
| 4,582,181 | 4/1986 | Samson | 128/348.1 |
| 4,597,755 | 7/1986 | Samson et al. | 604/96 |
| 4,601,706 | 7/1986 | Aillon | 128/673 |

FOREIGN PATENT DOCUMENTS

| | | | |
|---|---|---|---|
| 654214 | 2/1986 | Switzerland | 604/101 |
| 1499520 | 2/1975 | United Kingdom | |

OTHER PUBLICATIONS

Steerable Step-Up Balloon; Product Literature of Schneider Medintag.
Owens Balloon Dilatation Catheter; Product Literature of Mansfield.
Trefoil Meier Valvuloplasty Set; Product Literature of Schneider Medintac.
Valvuloplasty Dilatation Catheter; Product Literature of Schneider Gruntzig.
Culling W. et al.; Percutaneous Transluminal Valvuloplasty; *The Lancet;* 1986; 1:909.
Sievert H. et al.; Perkutane Valvuloplastik der Aortenklappe im Erwachsenenalter; *DMW;* 1986; 13:504-06.
Balloon Relieves Pulmonary Valve Stenosis; *THI Today;* 1986:12-13.
Rupprath, G. et al.; Percutaneous Balloon Valvuloplasty for Aortic Valve Stenosis in Infancy; *Am. J. of Cardiology;* 1984; 3:1655-56.
Sanchez, G. R. et al.; Successful Percutaneous Balloon Valvuloplasty of the Aortic Valve in an Infant; *Pediatric Cardiology;* 1985; 6:103-06.
Macaya C. et al.; Valvuloplastia transluminal percutanea con cateter-balon en la estenosis congenita de la valvula aortica; *Revista Espanola de Cardiologia:* 1985; 38:396-99.

(List continued on next page.)

*Primary Examiner*—Dalton L. Truluck

[57] ABSTRACT

Dilatation procedures and catheter instrument for treating patients having acquired aortic stenosis, typically in which there are calcific deposits on the leaflets of the aortic valve. A dilatation balloon introduced into the stenosed aortic valve via the aorta while the blood circulation of the patient is maintained by the heart via the aortic valve, is inflated to grossly deflect the leaflets of the valve in a manner avoiding blocking the outer portions of the commissures of the valve. This inflating step enables substantial flow of blood through the outer portions of the commissures during systole despite the presence in the valve of the large inflated balloon. By prolonging the inflation for at least 30 seconds, over a large multiplicity of heart beats the calcific deposits are disturbed to increase the pliability of the leaflets and the degree of their opening, in an action found not to produce emboli. The catheter instrument incorporates means for measuring the pressure gradient across the valve and has features facilitating introduction, retention of position during inflation, withdrawal and recrossing of the valve to achieve progressive enlargement of the aortic valve.

40 Claims, 6 Drawing Sheets

OTHER PUBLICATIONS

Waller, B. F. et al.; Transverse Aortic Wall Tears in Infants After Balloon Angioplasty for Aortic Valve Stenosis: *J. Am. Coll. Cardiology;* 1984; 4:1235–41.

Mindich, B. P.; Aortic Valvuloplasty for Acquired Aortic Stenosis; *Am. Heart Assn.,* 1985; 3:209.

Neuhaus, K. L. et al.; Valvuloplastie und periphere Angioplastie mit Koronardilatationshkathetern; *DMW;* 1985; 18:703–08.

Lababidi, Z.; Aortic Balloon Valvuloplasty; Am Heart Journal; 1983; 106:751–52.

Lababidi, Z. et al.; Percutaneos Balloon Aortic Valvuloplasty: Results in 23 Patients; *Am. J. Cardiology,* 1984; 53:194–97.

Walls, J. T. et al.; Assessment of Percutaneous Balloon Pulmonary and Aortic Valvuloplasty; *J. Thorac. Cardiovasc. Surg.;* 1984; 88:352–56.

Brockmeier, L. B. et al.; Calcium Emboli to the Retinal Artery in Calcific Aortic Stenosis; *Am. Heart J.,* 1981; 101:32–37.

Rees, J. et al.; Thoracic and Cardiovascular Surgery; Aortic Valvuloplasty for Stenosis in Adults; *Am. Assoc. Thorac. Surg.;* 1974; 67:390–94.

Weinstein G. S. et al.; Aortic Valvuloplasty for Calcific Aortic Stenosis in the Adult; *J. Cardiovasc. Surg.;* 1980; 21:675–80.

Walls, J. T. et al.; Assessment of Percutaneous Balloon Pulmonary and Aortic Valvuloplasty; *J. Thorac. Cardiovasc. Surg.,* 1984; 88:352–56.

Inoue, K, et al.; Clinical Application of Transvenous Mitral Commissurotomy by a New Balloon Catheter; *J. Thorac. Cardiovasc. Surg.,* 1984; 87:394–402.

Cohen, M. V. et al.; Modified Orifice Equation for the Calculation of Mitral Valve Area; *Am. Heart J.,* 1972; 84:839.

Rocchini, A. P. et al.; Percutaneous Balloon Valvuloplasty for Treatment of Congenital Pulmonary Valvular Stenosis in Children; *J. Am Coll Cardiol,* 1984; 3:1005–12.

Lababidi, Z. et al.; Percutaneous Balloon Aortic Valvuloplasty: Results in 23 Patients; *Am. J. Cardiol.,* 1984; 53:194–97.

Lock, J. E. et al.; Balloon Dilatation Angioplasty of Hypoplastic and Stenotic Pulmonary Arteries; *Circulation,* 1983; 67, 5:962–7.

Labibidi, Z. et al.; Percutaneous Balloon Pulmonary Valvuloplasty; *Am. J. Cardiol.* 1983; 52:560–62.

Pepine, C. J. et al.; Percutaneous Balloon Valvuloplasty for Pulmonic Valve Stenosis in the Adult; *Am. J. Cardiol,* 1982; 50:1442–45.

Rey, C. et al.; Valvuloplastie transluminale percutanee des stenoses pulmonaires; A propos de 24 cas, *Arch Mal Cocur,* 1985; 78:703–10.

Cooper, R. S. et al. Balloon Dilatation Angioplasty: Nonsurgical Management of Coarctation of the Aorta; *Circulation,* 1984; 70:903–07.

Kan, J. S. et al.; Percutaneous Transluminal Balloon Valvuloplasty for Pulmonary Valve Stenosis; *Circulation,* 1984; 69:554–60.

PROCEDURE AND CATHETER INSTRUMENT FOR TREATING PATIENTS FOR AORTIC STENOSIS

BACKGROUND OF THE INVENTION

This invention relates to an aortic valve dilatation instrument and treatment useful for adult patients having aortic stenosis, especially acquired calcific stenosis, a disease which is prevalent in elderly people.

Stenosis of the aortic valve has long been known to cause serious diminishment of blood flow from the heart. The critical position of the aortic valve, preceding the arteries that nourish the heart and brain as well as all other parts of the body, makes this a very serious ailment.

For those patients sufficiently well to endure the surgery, it has become common to replace the aortic valve with a prosthetic device while the patient is maintained by an extra-corporeal circulation system that by-passes the heart and valve. There is, however, risk with this major surgical procedure and there remains a large population who are too weak or otherwise do not wish to undergo such surgery.

RELATIONSHIP TO PRIOR TECHNIQUES

Percutaneous transluminal balloon catheter angioplasty is a recognized treatment for peripheral and coronary artery stenoses. This technique has also been used successfully in certain forms of coarctation of the aorta, pulmonary stenosis, congenital aortic valve stenosis, and mitral stenosis, but not previously in adults with acquired aortic valve stenosis. It might be thought impossible to dilate such long-standing and usually calcified lesions because of the anticipated critical effects of the expected disruption of the aortic blood flow in the weakened patient and the apparently serious risk of dislodging particles of the calcific plaque to produce life-threatening emboli in the blood stream.

References to work prior to commencement of our development are:

Cooper, R. S.; Ritter, S. B.; Golinko, R. J.; Balloon dilatation angioplasty: Nonsurgical management of coarctation of the aorta; *Circulation*, 1984; 70:903-07.

Kan, J. S.; White, R. I.; Mitchell, S. E.; Anderson, J. H.; Gardner, T. J.; Percutaneous transluminal balloon valvuolplasty for pulmonary valve stenosis; *Circulation*, 1984; 69:554-60.

Lababidi, Z.; Wu, J. R.; Percutaneous balloon pulmonary valvuloplasty; *Am J. Cardiol*, 1983; 52:560-62.

Pepine, C. J.; Gessner, I. H.; Feldman, R. L.; Percutaneous balldon valvuloplasty for pulmonic valve stenosis in the adult; *Am. J. Cardiol*, 1982; 50:1442-45.

Rey, C.; Marache, P.; Matina, D.; Mouly, A.; Valvuloplastie transluminale peructanee des stenoses pulmonaires; A propos de 24 cas, *Arch Mal Cocur*, 1985; 78:703-10.

Rocchini, A. P.; Kveselis, D. A.; Crowley, D.; Dick Mac, D.; Rosenthal, A.; Percutaneous balloon valvuloplasty for treatment of congenital pulmonary valvular stenosis in children; *J. Am. Coll Cardiol*, 1984; 3:1005-12.

Lababidi, Z.; Wu, J. R; Walls, J. T.; Percutaneous balloon aortic valvuloplasty: results in 23 Patients; *Am. J. Cardiol*, 1984; 53:194-97.

Lock, J. E.; Castaneda-Zuniga, W. R.; Fuhrman, B. P.; Bass, J. L.; Balloon dilation angioplasty of hypoplastic and stenotic pulmonary arteries; *Circulation*, 1983; 67, 5:962-7.

Walls, J. T.; Lababidi, Z.; Curtis, J. J.; Silver, D.; Assessment of percutaneous balloon pulmonary and aortic valvuloplasty; *J. Thorac. Cardiovasc. Surg.*, 1984; 88:352-56.

Inoue, K.; Owaki, T.; Nakamura, T.; Kitamura, F.; Miyamoto, N.; Clinical application of transvenous mitral commissurotomy by a new balloon catheter; *J. Thorac. Cardiovasc. Surg.*, 1984; 87:394-402.

Cohen, M. V.; Gorlin, R.; Modified orifice equation for the calculation of mitral valve area; *Am. Heart J.*, 1972; 84:839.

Brockmeier, L. B.; Adoph, R. J.; Gustin, B. W.; Holmese, J. C.; Sacks, J. G.; Calcium emboli to the retinal artery in calcific aortic stenosis; *Am. Heart J.*, 1981; 101:32-37.

SUMMARY OF THE INVENTION

In the beginning of our work (Cribier and Letac), percutaneous transluminal balloon catheter aortical valvuloplasty (PTAV) was carried out in three elderly patients with acquired severe calcific aortic valve stenosis. In all 3 cases, severity of progression made valve replacement appear both mandatory and urgent. We elected to attempt valvuloplasty, however, because advanced age and poor physical condition made the operative risk very high in 2 patients, while the third refused to contemplate surgery. Transvalvular systolic pressure gradient was considerably decreased at the end of each procedure, during which there were no complications. Increased valve opening was confirmed by a decrease in pressure gradient and an increase in valve area, calculated by Gorlin's formula using measurement of cardiac output. Subsequent clinical course showed a pronounced functional improvement. (For simplicity, in the following text, measured pressure gradient will be used to denote the results.)

In the course of this work, and confirmed by many follow-up cases, it has been discovered that placement of an appropriately sized inflated balloon in an aortic valve that is seriously stenosed as a result of calcific plaque build-up, does not, in the majority of cases, significantly worsen blood flow through the stenosed valve during a prolonged treatment (greater than thirty seconds, up to four minutes); that dilatation and in particular prolonged dilatation provides a very desirable increase in pressure-responsiveness of the valve leaflets to produce a larger arterial flow; that the calcific plaque, though effectively disturbed by the dilatation does not result in significant entry of free particles in the vascular system, so that life-threatening calcific emboli are not generally formed; and we have confirmed, by correlation with measured cardiac output, that measurement of pressure gradient across the valve, even with a catheter present in the valve, is useful as one indication of the improvement achieved by the procedure.

As a further, very important aspect of the invention, we (Cribier and Letac) have conceived a multipurpose aortic valve dilatation catheter, and procedure using it, that significantly reduces the number of procedural steps, reduces the time required for the procedure, and enhances patient safety. The final design (to which Ariola contributed) has been demonstrated to facilitate re-entry into the valve for repeated dilatation of the aortic valve without need of a guidewire, to enable monitoring of the results at each step, and to enable ventriculograms, aortograms, and angiograms of the left coronary artery. Use of the device significantly reduces trauma to the blood vessels, and provides significant improvement in patient comfort.

Certain features of the invention are summarized in more detail as follows:

A dilatation procedure for treating patients having calcific aortic stenosis, in which there are calcific deposits on the leaflets of the aortic valve that impair their opening movement during systole, comprising the steps of: introducing a dilatation balloon into the stenosed aortic valve via the aorta while the blood circulation of the patient is maintained by the heart via the aortic valve, inflating the balloon to grossly deflect the calcific leaflets of the valve in a manner avoiding blocking the outer portions of the commissures of the valve, the inflating step enabling substantial blood flow through the outer portions of the commissures during systole despite the presence in the valve of the inflated balloon, and prolonging the inflation of the balloon over an interval spanning a large multiplicity of heart beats, e.g. thirty seconds or longer, whereby the calcific deposits on the leaflets are disturbed to increase the pliability of the leaflets and the degree of their opening in response to systolic pressure, the calcific deposits, though thus disturbed by the dilatation, remaining as part of the leaflets so that life-threatening emboli do not form. In this manner, while grossly deflected by the balloon, the leaflets may be repeatedly, oppositely stressed by exposure to alternating systolic and diastolic pressure conditions to improve their action.

In carrying out the above procedure there are a number of preferred further features: the inflation of the balloon is so performed that, during the inflation, the calculated effective flow cross-section in the unblocked outer portions of the commissures during systole is of the order of or greater than the calculated flow cross-section during systole of the stenosed valve prior to the dilatation; where the treatment is of a normally sized adult, the balloon is selected to have an average inflated diameter in the range between about 14 and 24 mm; the interval of prolonged inflation is preferably of the order of one minute or more and preferably no greater than about 5 minutes; the aortic pressure is monitored during the inflation and the inflation is discontinued upon the occurrence of substantial decrease in aortic pressure during systole; prior to inflation of the balloon in the valve, the pressure gradient is measured across the aortic valve in the absence of the balloon within the valve, to establish a pre-dilatation base-line value for the flow-restriction imposed by the stenosed valve, and during the procedure, following inflation of the balloon within the valve, the balloon is withdrawn from the valve, the pressure gradient is re-measured, and the procedure is terminated when the gradient has substantially decreased, e.g., to about 30 mm Hg or less; preferably these pressure gradients being measured while a distal portion of the balloon catheter is within the valve; a multilumen dilatation catheter is provided having at least two pressure-measuring lumens in addition to lumen means that inflates the balloon, one of the pressure-measuring lumens terminating in distal sensing port means disposed on the portion of the catheter distal of the balloon, the sensing port means adapted for measuring pressure in the left ventricle of the heart, and a second of the pressure-measuring lumens terminating in a proximal sensing port means disposed along the catheter proximal of the balloon, the second sensing port means adapted for measuring aortic pressure, the distal sensing port means being spaced distally from the balloon a distance sufficient that, while the balloon resides proximal of the aortic valve, the distal portion of the catheter extending through the valve can position the distal sensing port means entirely within the left ventricle of the heart, the procedure including the step of positioning the catheter so that the balloon lies proximal of the valve and the distal sensing port means lies entirely within the left ventricle, and while the catheter is thus disposed, by use of the distal and proximal sensing port means, measuring the pressure gradient across the valve while the heart is beating, and the procedure including the step of positioning and inflating the balloon within the valve to cause the gross deflection of the valve leaflets; a dilatation balloon catheter is provided having a curved distal portion of a stiffness no greater than a first value over a length extending from the distal tip of the catheter to a point close to but distal of the balloon and having a second portion of substantially greater stiffness extending from the point, proximally at least to a point beyond the portion of the catheter that lies in the aortic arch during inflation of the balloon and preferably for the full length of the catheter to enable the physician to grasp and thrust or twist the catheter without disadvantageous distortion of the catheter, the distal portion adapted to flex and follow a guidewire over which it is threaded to pass through the aortic valve and into the left ventricle, and to conform atraumatically to the wall of the ventricle while the heart is beating, and the second, relatively stiffer portion of the catheter serving to resist collapse under axial compression to enable repeated thrusting of the balloon into the valve, and, by reaction of the catheter against the wall of the aortic arch, to hold the balloon in axial position within the valve during inflation while the balloon is confronted by pressurized flow of blood from the heart; during withdrawal the catheter tip is designed to rake across or be manipulated to register with the coronary artery to permit injection of radiopaque contrast fluid.

According to a further aspect of the invention, a method of aortic valvuloplasty, comprises:

A. providing an inflatable balloon catheter selected to have an effective balloon size and shape to deflect valve leaflets without occluding the outer portions of the commissures, the balloon catheter having a relatively flexible, curved distal portion defining a conduit that has a multiplicity of side holes for measurement of pressure and injection of fluid, a relatively stiff distal segment of catheter substantially smaller than the balloon disposed between the flexible curved distal portion of catheter and the balloon, and an elongated catheter body proximal of the balloon and defining an opening proximal of the balloon for measurement of pressure;

B. advancing the balloon catheter until the distal flexible portion is passed through the valve into the ventricle, and the distal stiff segment of catheter is lodged within the valve, blood flow through the valve being only minimally impeded because of the relatively small diameter of the stiff segment;

C. measuring the pressure in the ventricle by means of the openings in the flexible distal catheter portion and measuring the pressure in the aorta by means of the proximal opening to determine the pressure gradient across the valve, such gradient being minimally affected by the presence of the small diameter, stiff segment of the catheter within the valve;

D. advancing the catheter until the balloon is positioned within the valve;

E. inflating the balloon to deflect the leaflets of the valve;

F. deflating the balloon and withdrawing the balloon catheter until the stiff segment is again lodged within the valve;

G. repeating step C to determine the pressure gradient resulting from the treatment; and H. removing the balloon catheter from the patient.

In prefered embodiments, the method includes, after withdrawing the balloon as provided in step G, thrusting the balloon forward to cause the stiff segment to guide the balloon back into the valve, and thereafter repeating steps E, F and G before removing the catheter from the patient; the method further includes, during the inflation of the balloon, continually monitoring the aortic pressure and deflating the balloon and withdrawing it from the valve upon the occurrence of significant drop in aortic pressure, preferably the method further comprises, where desirable, repeating steps E through G until an acceptable pressure gradient is achieved, and preferably the method further includes continually monitoring aortic pressure and, under the conditions that the aortic pressure has not significantly dropped and pressure differential across the valve has remained above about 30 mm Hg, repeating steps E, F and G; the balloon is of stepped construction of two different diameters, with the smaller diameter portion positioned distally of the larger diameter portion, and the method comprises dilating the valve with the smaller diameter balloon portion and then dilating the valve with the larger diameter portion; the method further comprises the step of taking a ventriculogram by injecting a radiopaque contrast fluid through openings of the flexible distal portion while the distal portion is positioned in the ventricle and the small diameter stiff segment is lodged within the valve; the method comprises withdrawing the distal portion of the catheter through the valve, into the aorta, injecting radiopaque contrast fluid via the distal opening of the catheter into the aorta and performing an aortogram; the method comprises, during removal of the balloon catheter, positioning the distal end of the catheter in the left coronary artery osteum and injecting radiopaque contrast fluid via the distal opening of the catheter into the coronary artery for performing a coronary angiogram; and the catheter is provided with a bend of about 30° proximal of, but adjacent to, the balloon, the method comprising performing initial diagnostic catheterization of the aortic stenosis using the balloon catheter and a guidewire inserted from the aorta through the valve, over which the balloon catheter is passed, the bend facilitating the passage of the catheter over the guidewire, through the aorta and the valve.

The invention also features aortic valvuloplasty dilatation catheters per se, constructed as described above.

Such catheters preferably have a number of further important preferred features: the first portion of the catheter incorporates a single lumen adapted to slide over a guidewire and to serve for measurement of ventricular pressure and the second portion of the catheter incorporates that lumen and at least two additional lumens, one of which is adapted for measurement of aortic pressure and another of which is adapted for inflation of the balloon; the two portions of the catheter are integral, the first portion of the catheter being the product of heating and radial collapsing of a multiple lumen catheter of thermoplastic while only the single lumen is supported by a mandrel residing within the lumen; a stiffener rod is permanently embedded within the catheter, the rod extending distally to the point lying distal of the balloon, preferably the distal tip of the rod being fixed with respect to the catheter, proximal portions of the rod being free to slide in the lumen relative to the catheter in response for instance to bending of the catheter and/or preferably an extended sleeve integral with the balloon extends distally of the balloon a distance of between about 1 and 2 centimeters, serving to stiffen the corresponding portion of the catheter.

In any of the aortic valvuloplasty dilatation catheters above, the balloon preferably has a number of other preferred features: it is of stepped construction having at least two different diameters and has tapered transition portions, preferably, in a two diameter balloon the smaller diameter portion of the balloon comprising the distal portion of the balloon being between about 2 and 2.5 cm in length and having a diameter between about 14 and 18 mm and the larger diameter portion of the balloon comprising the proximal portion of the balloon being between about 3 and 3.5 cm in length and having a diameter between about 18 and 24 mm, the tapered transition portions at the ends of the balloon having a length between about ½ and 1 cm and the transition between the two balloon diameters being of the order of ½ cm in length; a bend in the catheter is provided of between about 20° and 30°, located immediately proximal of the balloon and adapted to ease the passage of the catheter through the aortic arch; the distal portion of the catheter has a compound curvature, the distal-most portion having a smaller radius of curvature than the portion lying proximal thereof, preferably the total arc of the curvature being between about 200° and 250°, the catheter adapted, when the distal tip is withdrawn into the aorta from the valve, to register with the inlet of a coronary artery to enable injection of radiopaque contrast fluid therein, whereby an angiogram of the coronary artery can be obtained; the catheter has a distribution of side holes along the length of the distal portion, on the inside of the curve, the proximal-most hole being at least about 3 cms distal of the end of the balloon, for the purpose of left ventricular angiography before the valvuloplasty procedure and supravalvular aortograms; each hole has a flow cross-sectional area between about 1.5 to 2.0 mm$^2$; there is provided a further hole at the end of the distal portion the further hole having a flow cross-sectional area substantially greater than that of any of the side holes; in one instance, the balloon is cylindrical and has a diameter between about 14 and 24 mm and is about 3½ to 4½ cm in length; in another instance, the balloon is of noncircular cross-section having a multiplicity of lobes for the purpose of enhancing blood flow past the balloon; and the catheter further comprises a pair of spaced apart radiopaque indicators positioned on the catheter, distal of the balloon, to enable the physician to accurately determine the position of the portion of the catheter relative to the valve when the balloon is withdrawn from the valve, with one of the markers lying on each side of the valve.

Other features and advantages of the invention will be understood from the following description of the original case reports and the presently preferred embodiments, and from the claims.

INITIAL CASE REPORTS

Case 1

A 77 year old woman had been treated for 10 years for angina pectoris. In August, 1984 several syncopal attacks on mild exertion led to the discovery of aortic stenosis. Angina and exertional dyspnoea severely limited physical activity. physical examination showed a mid-systolic grade 3/6 murmur at the aortic area, radiating to the cervical vessels, an absent second heart sound, and a grade 1/6 diastolic murmur. Electrocardiogram (ECG) showed pronounced left ventricular hypertrophy, and the left ventricle was moderately enlarged on the chest radiograph. Two-dimensional (2D) echocardiogram showed severe aortic stenosis with calcifications and satisfactory left ventricular function. In view of the severity of symptoms, cardiac catheterization was proposed for preoperative evaluation, but the patient withheld her consent for a year, during which symptoms steadily worsened, with nocturnal angina and two episodes of syncope at rest.

Left ventricular catheterization showed left ventricular pressures of 245/28 mm Hg and aortic pressures of 155/70 mm Hg (systolic pressure gradient 90 mm Hg). Aortic valve cusps were moderately calcified. Selective left ventricular angiography showed a normal diastolic volume (73 ml/m$^2$), with normal left ventricular function (ejection fraction 775) and clearly thickened walls. Post-stenotic dilatation of the ascending aorta and slight aortic regurgitation were seen on aortic angiography. Selective coronary arteriography did not show any significant coronary lesions. The patient gave informed consent for PTAV as an alternative to surgical valve replacement and this was done three weeks later.

Case 2

A 68 year old woman had had aortic stenosis diagnosed 15 years previously. Her clinical status deteriorated progressively over the years (New York Heart Association functional class III) and angina appeared and became progressively worse. Admission for further investigation was precipitated by an attack of severe chest pain when walking against the wind, followed by syncope. Physical examination on admission showed a grade 3/6 systolic murmur at the base, absent second heart sound, and a grade 2/6 diastolic murmur. There were clearcut signs of left ventricular hypertrophy on ECG and the chest radiograph showed slight cardiomegaly. 2D echocardiogram showed severe calcific aortic stenosis with normal left ventricular function.

Cardiac catheterization demonstrated ventricular pressures of 230/22 mm Hg and aortic pressures of 100/50 mm Hg (systolic pressure gradient 130 mm Hg). The aortic valve was massively calcified. Right heart pressures and cardiac index were normal. Left ventricular angiography showed a normal end-diastolic volume (94 ml/m$^2$) with slightly reduced ejection fraction (54%) and thickened walls. The ascending aorta was moderately dilated, and aortic regurgitation was insignificant. Selective coronary arteriogram was normal.

Severity of both symptoms and haemodynamic data led us to propose immediate valve replacement, but the patient would not contemplate surgery. However, she accepted PTAV, which was done a month later.

Case 3

A 79 year old man had complained of progressive exertional dyspnoea for 10 years was admitted after three syncopal attacks brought on by mild exertion. Aortic stenosis was diagnosed. Physical examination on admission showed a grade 4/6 mid-systolic murmur at the base, with an absent second heart sound. ECG showed severe left ventricular hypertrophy and the chest radiograph mild cardiomegaly and signs of mild pulmonary hypertension. 2D echocardiogram showed severe aortic stenosis with considerable valve calcification and severe left ventricular dilatation with impaired ventricular function. Too days after admission, the patient had an episode of acute, massive pulmonary oedema which was brought under control with difficulty by high doses of frusemide.

At cardiac catheterization, left ventriculiar pressure was 140/28 mm Hg (systolic pressure gradient 60 mm Hg) and the aortic valves were massively calcified. Left ventricular angiography confirmed left ventricular dysfunction, with an increased diastolic volume (190 ml/m$^2$) and greatly decreased ejection fraction (20%). Selective coronary arteriography showed major multiple vessel lesions with proximal left-anterior-descending occlusion. These findings made us reluctant to recommend valve replacement and, with information consent, we decided to attempt PTAV.

METHODS

The same procedure for PTAV was followed in all 3 patients. Premedication consisted of intravenous atropine sulphate 1 mg, clorazepate 50 mg, and heparin 100 u/kg bodyweight. A surgical team was on standby.

For continuous aortic pressure monitoring, a 5F catheter was inserted into the descending thoracic aorta. In addition, a Swan-Ganz thermodilution catheter was inserted into the pulmonary artery in patients 2 and 3 for measurement of cardiac output. Left ventricular catheterization was carried out via the brachial approach which made it easier to cross the stenosed aortic orifice (and was also necessitated by the short length (60 cm) of the dilatation catheters available in our laboratory). A 7F Sones catheter was inserted into the aorta and then in the left ventricle. After simultaneous left ventricular and aortic pressure recording, right-anterior-oblique angiograms of the left ventricle and of the aortic root were done. A Cordis straight guidewire, diameter 0.038 inch, length 270 cm, was inserted into the left ventricle via the Sones catheter to enable its replacement by the dilatation catheter.

We used 9F balloon catheters designed for dilatation of congenital valve stenosis, available from Meditech, Incorporated, of Watertown, Mass. and from Mansfield Scientific, Inc. of Mansfield, Mass. Two radiopaque markers gave the positions of the distal and proximal ends of the balloon, thus ensuring correct transvalvular positioning which was also confirmed by narrowing of the balloon where it crossed the stenosis during inflation. The balloons were 40 mm long. Inflations were carried out by injecting 10 ml of a 50/50 mixture of saline solution and contrast medium, up to pressures of 6–8 atm. Three inflations, lasting 20–60s, were successively done with three balloons whose maximum inflatable diameters were 8, 10, and 12 mm, respectively. In order to stabilize the balloon in its transvalvular position, the guidewire was left in the ventricular cavity during inflation.

ECG and aoriic pressure were continuously recorded during the procedure. Ventricular and aortic pressures were simultaneously measured after each series of inflations. At the end of the procedure, an aortic root angiogram was done to assess valve opening and residual aortic regurgitation.

RESULTS

The haemodynamic and clinical response to the inflations was good. There was no loss of consciousness when the balloon was inflated in transvalvular position. The first patient complained of moderate chest pain after 15–20 s of inflation, at the same time an ST-segment depression was noted in the antero-lateral precordial leads. In patients 2 and 3 the three inflations each lasted 1 min. without any ill-effects.

During inflation, the aortic pressure never decreased below 60 mm Hg. The obstruction caused by the inflated balloon was therefore incomplete; this was confirmed by manual injection of a few ml of contrast medium into the ventricular cavity during one inflation (via the angioplasty catheter with guidewire removed). A few premature ventricular contractions occurred infrequently during the inflations.

In the first patient, transvalvular gradient was 90 mm Hg at the start of the procedure and remained unchanged after the first two series of inflations with the 8 and 10 mm balloons. After a series of these inflations with the 12 mm balloon, it decreased to 40 mm Hg. In the second patient, the mitral gradient was found to be 80 mm Hg (rather than the 130 mm Hg measured during the initial catheterization) and decreased to 70, 60 and finally 30 mm Hg after each series of inflations. In the third patient, improvement of systolic gradient was very similar—from 60 mm Hg to 50, 40, and finally 30 mm Hg. In patients 2 and 3 in whom cardiac output was measured before and after valvuloplasty, valve surface calculated according to Gorlin's formula increased from 0.46 cm to 0.96 cm$^2$ and from 0.50 cm$^2$ to 0.75 cm$^2$, respectively.

Aortic root angiography showed no worsening of the aortic regurgitation. Valve motion, which was considerably impaired before the procedure, was greatly improved, especially in the second patient. These results were supported by the findings of 2D echocardiography done 24 hours later in the patasternal long axis view, opening of the aortic valve increased from 0.45 to 0.77 cm in the first case, from 0.41 to 0.72 cm in the second (FIG. 4); and from 0.32 to 0.48 cm in the third. In the cross-sectional view, valve opening was also clearly improved, mainly in the second patient.

Clinical course during the eight days in hospital after the procedure was uneventful in the first two patients, and before discharge both climbed three flights of stairs without any pain or displayed a striking functional improvement. At four weeks, the improvement persisted, there had been little pain, and very little dyspnoca, even though the patients had by then resumed a normal lifestyle. Follow-up of the third patient has been shorter, but it was uneventful after fifteen days with no more functional signs, including dyspnoca.

DISCUSSION

To our knowledge, the 3 patients reported here are the first to undergo PTAV of adult acquired aortic stenosis. Immediate results appear very encouraging, since the dilatation resulted in a change from severe to moderate aortic stenosis according to the usual haemodynamic criteria—a pronounced decrease in the ventriculo-aortic systolic pressure gradient, with a residual gradient of 40 mm Hg in one patient, and of 30 mm Hg in the other two.

From the angiographic and echocardiographic data, improvement in the gradient is a consequence of better systolic valve opening. The balloon inflations probably resulted in a partial tear of the stenosed valve. Although the valve orifice is often hard to cross in severe adult calcific aortic stenosis, we experienced no technical difficulty in passing the dilatation catheters via the aortic orifice and in reaching a good transvalvular position. The excellent patient tolerance of the inflations is worth emphasizing, since we had feared that inflation of the balloon in a stenosed aortic orifice might lead to syncopal circulatory arrest. During the inflations, the aortic pressure remained satisfactory, suggesting that the inflated balloon was not totally occlusive, probably due to the irregular shape of the aortic orifice. There were no complications during or after the procedure, although calcium embolism could be considered a risk.

These 3 cases, and a large number of further cases using larger balloons and longer durations of inflation illustrate the feasability of the general procedure, its good patient tolerance, and the resulting haemodynamic and clinincal improvement. PTAV can offer a simple therapeutic alternative to patients, mostly elderly, in whom surgery would be to risky or impossible.

PREFERRED EMBODIMENTS OF THE AORTIC VALVULOPLASTY CATHETER

We first briefly describe the drawings.
Drawings

FIG. 1a is an enlarged view of the distal portion of the catheter, while

FIG. 4 is a diagrammatic view of the human heart, with the left ventricle shown in section, while

FIGS. 5 through 14 are diagrammatic views of the human heart with the left ventricle, and the aortic valve and arch shown in section, during respective further steps of the procedure, while

FIG. 15 is a partial plan view of the distal portion of the balloon, taken on an enlarged scale, of another embodiment of the catheter of the invention, while

The aortic valvuloplasty dilatation catheter instrument 10 of the figures comprises a 9 French catheter of about 100 cm length formed as a multilumen extrusion of medium density polyethylene material. The catheter has three lumens over its proximal length, $L_p$. The largest lumen 14, which has a diameter in the main catheter body of about 1.30 mm, is a distal lumen, which runs the entire length of the catheter to distal tip 20, and is used for threading the catheter over a guidewire as well as for measuring distal pressure and infusion of fluids. Second lumen 12 is for balloon inflation-deflation and terminates at ports 26, 28, 30 within dilatation balloon 22. The third lumen 16 is a proximal pressure measuring lumen that terminates at a proximal port 32, about 4 mm long and 0.8 mm wide, situated approximately 10 cm proximal of the balloon, for measurement of pressure and infusion of fluids. Lumens 12, 16 have diameter of about 0.8 mm each.

The catheter has an extended curved distal portion, $L_d$, beyond the balloon of about 5 cm length, having four side holes 21, defined on the inside of the curve, each having diameter between about 0.025 to 0.030 inch. The closest hole is placed 3 cms from the balloon and the others are spaced distally therealong at about ½ cm intervals. This distal portion of the catheter is of compound curvature, as shown, with the distal-most part $L_t$ having the smallest radius, the total arc of curvature of portion $L_d$ being about 200°. The tip is thus shaped so it will rest inside the curve and present a nontraumatic surface to the inner lining of the heart. The side holes in the distal portion are designed for measurement of pressure inside the ventricle and also for injection of radiopaque contrast fluid for ventricular graphs at the end of the procedure. The multiple side holes protect against the possibility that one or more holes may become occluded by rubbing up against the wall of the heart and also enable the relatively viscous contrast fluid, when injected, to be dispersed evenly and in desirably large amounts.

The distance from the balloon of the first or most proximal side hole 21 is established to make it possible to deflate the balloon when within the valve, withdraw the balloon into the ascending aorta, leaving the most proximal hole 21 still within the ventricle beyond the valve, so that the pressures measured through the distal lumen are the ventricular pressures. These pressures are compared to the pressures measured through the proximal port 32 and lumen 12, these two measurements providing an accurate measurement of pressure gradient across the aortic valve.

Disposed about the catheter are bands 36, 38, 40 of radiopaque material which give the cardiologist an accurate radiographic image of the location of the balloon in relation to the aortic valve.

Figure 3:
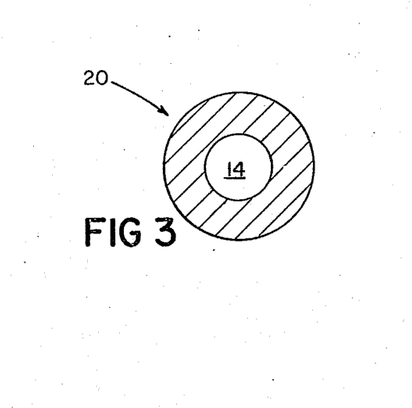

The distal portion of the catheter is drawn down to an outer diameter of about 7 French. The presently preferred manufacturing technique involves placing a mandrel in this portion of the distal lumen 14 while leaving the other lumens unsupported from within, heating the thermoplastic substance of this portion of the catheter and radially compressing the substance of the catheter to reform it about the mandrel, and cooling. This process closes the smaller lumens 12, 16 and reduces the diameter of the distal lumen 14 to about 1.12 mm, with the distal opening having a diameter of about 1 mm (FIG. 3). Thus the distal tip is made more flexible than the main body of the catheter, and is also made less traumatic to the wall of the ventricle and more able to easily follow the guidewire. The main body of the catheter is larger in outer diameter, e.g., about 3.05 mm, compared to the diameter of the distal portion, e.g., about 2.54 mm, giving the main body sufficient axial stiffness to permit the physician to push the balloon repeatedly through the aortic valve and providing a substantial resistance to torque so that the catheter may be twisted to facilitate insertion or to position the tip in a desired place, such as in the coronary artery during withdrawal for injection of contrast media for a coronary radiograph.

In this embodiment, the balloon itself has a thickness of 0.0035 inch and is formed of polyethylene that is biaxially oriented and treated to make it strong and noncompliant, with strength sufficient to withstand inflation pressures, of the order of 4 to 6 atmospheres, or higher (burst pressure of the order of eight atmospheres). The balloon is approximately 10 cm in length, and tapers gradually from the 9 French catheter shaft at the proximal end and the 7 French tip on the distal end to the full balloon diameter. The full diameter is different at the two ends of the balloon. On the distal end 42 there is a smaller balloon section, of 16 mm diameter and at the proximal end 44 there is a larger diameter balloon section of 20 mm diameter. The axial length of the distal portion 42 is between about 2 and 2½ cm and the length of the proximal portion 44 is between about 3 and 3½ cm. The tapered transition portions at each end of the balloon have lengths of one half up to one centimeter, and the transition between the two balloon diameters has a length of about one half centimeter.

The balloon terminates distally in a sleeve 43 which makes the corresponding portion of the catheter relatively more stiff than the tip portion to aid in the passage of the balloon when it crosses or re-crosses the valve. The tip portion itself is very flexible and is able to conform to the contours of the ventricle to which it is exposed. The distal sleeve 43 is between 1 and 2 cms in length and has a diameter of about 0.125 inch. The proximal sleeve 45 is curved at an angle between 20° and 30° to provide to the catheter a geometry which eases passage of the device through the aortic arch. The distal sleeve 43 and proximal sleeve 45 are integral continuations of the balloon, and serve to attach the balloon to the catheter itself. The balloon is attached to the catheter by heating the material of the sleeves and the underlying catheter to melt them together.

Percutaneous Technique

Figure 4:
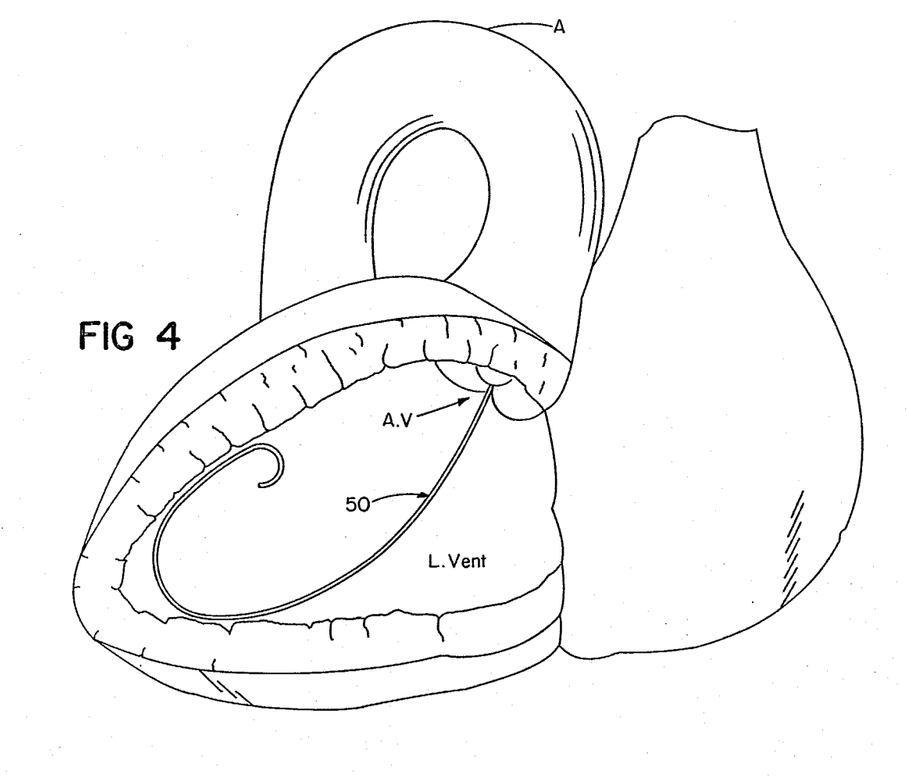
Figure 4A:
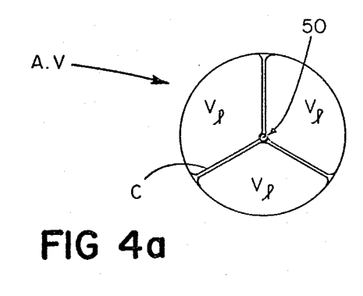
FIG. 4a is a schematic, axial view, on an enlarged scale, of the aortic valve as viewed from within the ventricle during the step of the procedure illustrated in FIG. 4.
Figure 5:
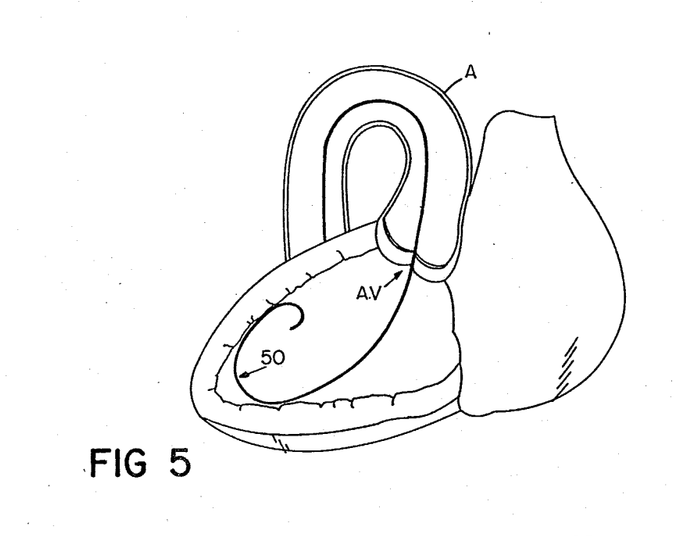

Employing the Seldinger technique for percutaneous insertion, a guidewire 50 is introduced into a puncture in the femoral artery of the patient and advanced through the aorta. The guidewire is advanced and allowed to coil inside the left ventricle (FIGS. 4, 4a, 5).

Figure 6:
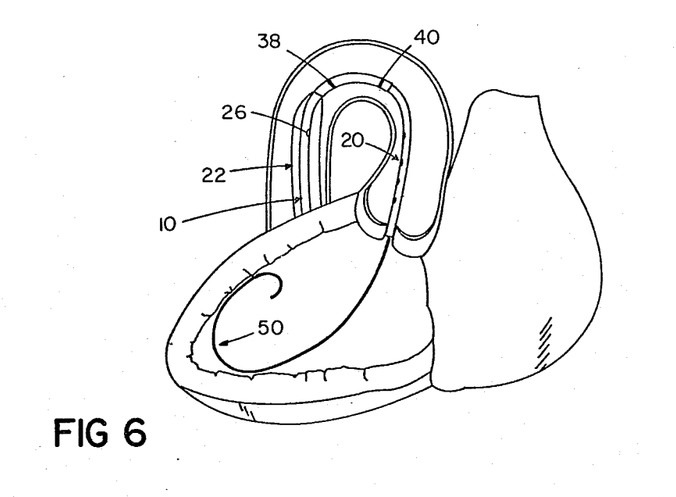
Figure 7:
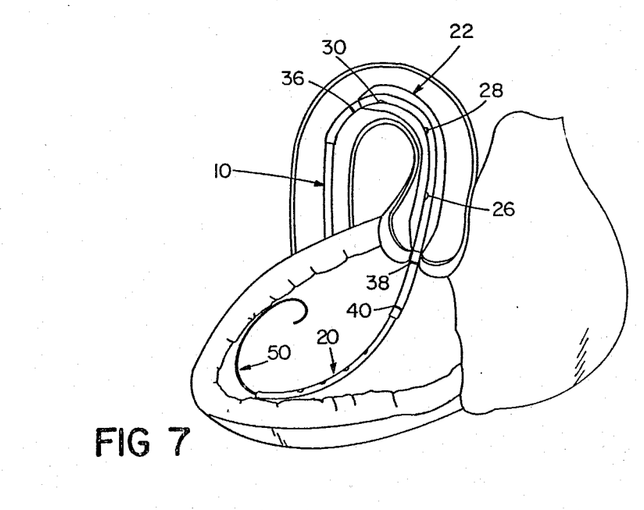
Figure 8:
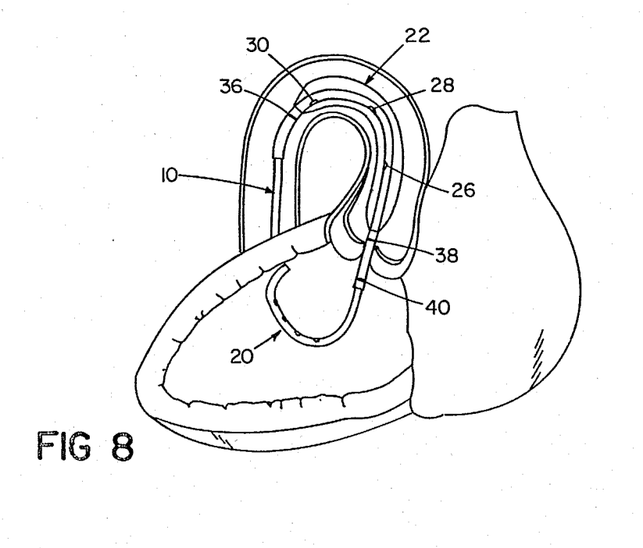
Figure 9:
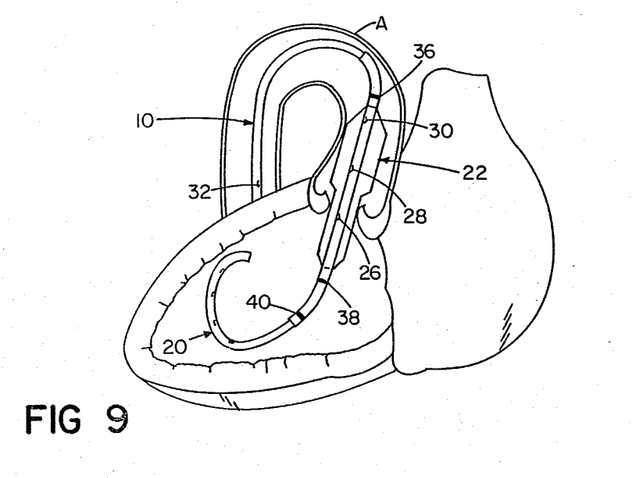
Figure 9A:
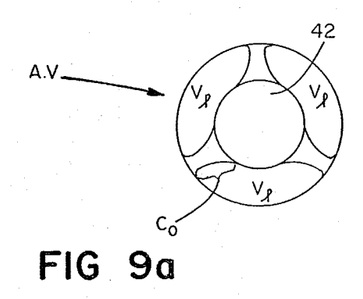
FIG. 9a is a schematic, axial view, similar to FIG. 4a, as viewed during the step of the procedure illustrated in FIG. 9.

The aortic valve dilatation catheter 10 of the invention is advanced along the guidewire, the leading portion of the catheter, conforming to the shape of the guidewire. The tip 20 is pushed through the aortic valve over the guidewire (FIG. 6). This is followed by the relatively stiff section of the sleeve 43 which helps to dilate the valve (FIG. 7). (The catheter may be preceded in these steps by a diagnostic catheter or the dilatation catheter 10 itself may be employed for diagnostic purposes.) The guidewire is withdrawn and the sleeve is positioned within the valve (FIG. 8), as determined by the physician observing the radiopaque rings 38, 40 at either side of valve AV. Also, prior to any portion of the balloon entering the valve, i.e., in the position of FIG. 8, but with the guidewire removed, when the holes 21 at the tip of the catheter are inside the ventricle and the proximal port 32 of the lumen is in the aorta, simultaneous pressures can be taken to enable the physician to obtain a pre-dilatation, base line pressure gradient across the valve by comparing the systolic peaks in the ventricle and aorta. A ventriculogram is then taken by injection of radiopaque fluid through the distal opening, and also via the side holes, with the physician observing the flow of the radiopaque fluid from the heart. When ready to commence dilatation, the physician, taking advantage of the relatively stiff sleeve lodged in the valve, advances the deflated balloon between the valve leaflets, $V_L$ (FIGS. 9, 9a). During this motion, the tip portion $L_d$ assumes its preset curve corresponding to the curved interior wall of the ventricle, the tip portion presenting a nontraumatic surface to the ventricle, the reduced diameter and added flexibility of the distal portion and its pre-set curve enabling this to occur with ease and without trauma to the ventricle wall.

Figure 10:
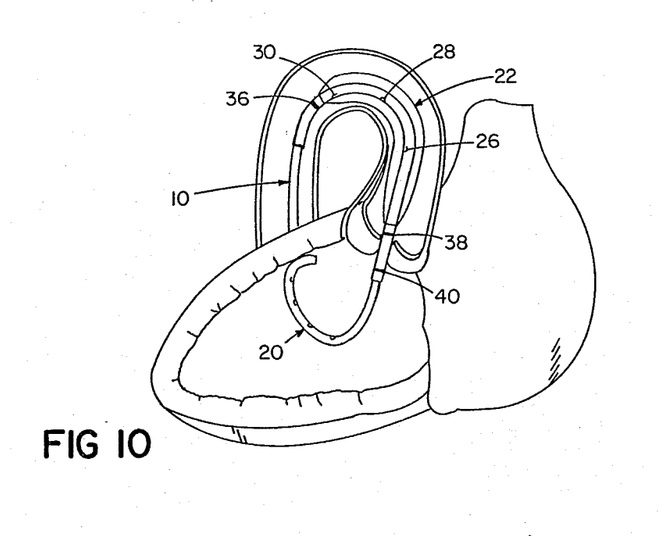

While aortic pressure is being monitored, the balloon is inflated with liquid and the valve is dilated with first the small diameter section of the balloon 42. After an interval, the balloon is deflated and withdrawn into a position where the tip of the catheter, including all the holes 21, remains inside the ventricle, with the balloon out of the valve, in the aorta, and the stiff sleeve is lying within the valve, FIG. 10.

Figure 11:
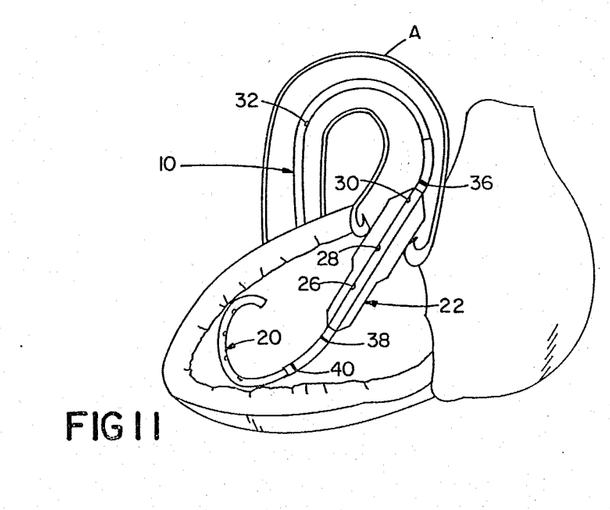

Pressures are again recorded through the distal and proximal lumens and the pressure gradient across the valve is determined. Depending upon the amount of this gradient, e.g., if it is above 30 mm Hg, the balloon is reinserted into the valve, facilitated by the stiff sleeve, without need to reinsert the guidewire (FIG. 11), this time the larger section of the balloon 44 being placed in the valve, and the balloon is again inflated.

Inflation of the balloon may be maintained from a few seconds (e.g., in the case of rapid decrease of aortic pressure) to many minutes, depending upon the condition of the patient. It is found, surprisingly, in a large majority of elderly and gravely ill patients, that despite the stenosed condition of the aortic valve, and the presence of the inflated balloon in the valve, the aortic pressure does not rapidly deteriorate. This is attributed to a special condition achieved at the commissures, C, the region of contact between the valve leaflets. It is found that when the inflated balloon is in place, the outer portions $C_o$ of the commissures C, open to provide a calculated flow cross sectional area commensurate with or even in some instances greater than the original stenosed calculated flow cross section of the valve.

Longer inflations tend to produce better results. As the heart beats, the valve in response to systolic and diastolic pressure conditions opens and closes around the relatively stiff surface of the highly inflated balloon, which is believed to disturb the calcium deposits in a manner increasing the pliability of the leaflets. Also, when a balloon is first inflated, it has been observed that there are indentations in the balloon in regions where the valve leaflets restrain the diameter of the balloon (so called "waisting" of the balloon). Sometimes a prolonged inflation and/or multiple inflations are required before this waisting action disappears, and the valve leaflets expand.

It has been found that a cylindrical shape of balloon is helpful in enabling the balloon to be left inflated for an extended period. This is attributed to the fact that a cylindrical balloon shape does not take up the space all the way to the root of the leaflets to block flow while it assures considerable distortion of the leaflets in their root region. This facilitates flow through the outer commissure regions $C_o$ held open by the balloon. During treatment, in making the valve leaflets more pliable, it is surmised that the calcium deposits on the leaflets are fractured or disrupted without dislodgement, which enables them to open wider and close more easily in response to the action of the heart, to provide better flow.

Figure 12:
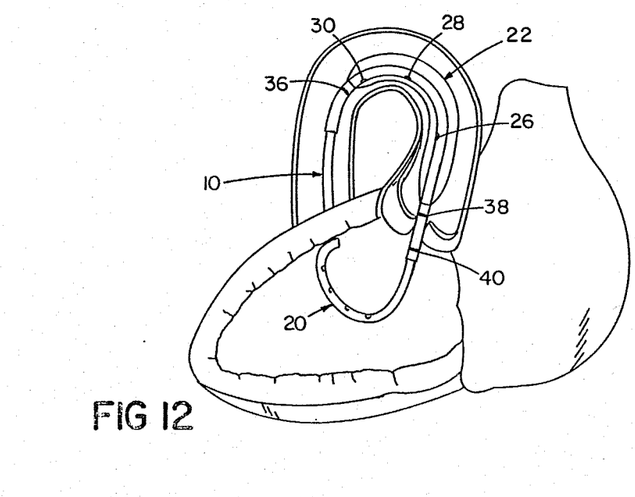
Figure 13:
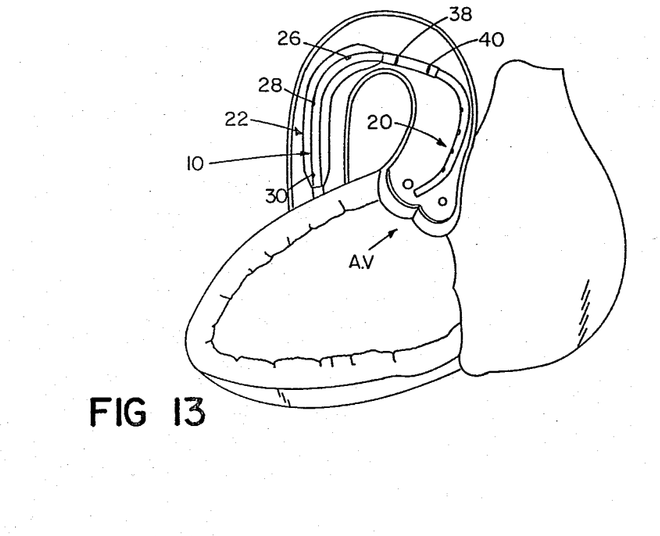
Figure 14:
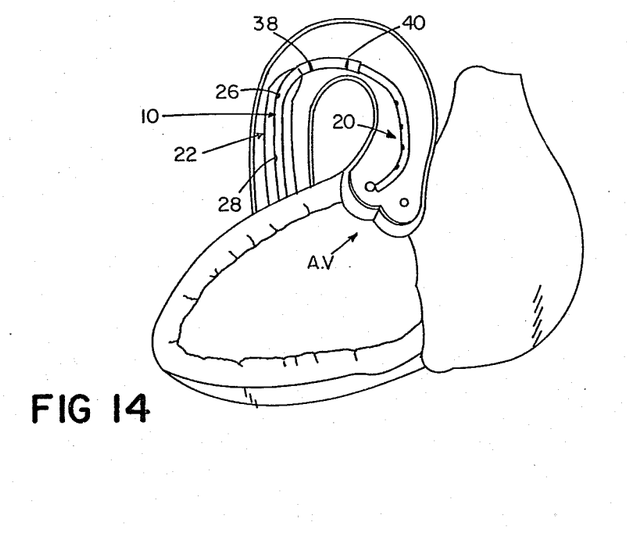

During the dilatation procedure, after the large section of the balloon has been expanded and the valve dilated, the balloon is again deflated. The balloon is again remove from the valve and, with the sleeve within the valve, the pressure gradient again measured between the aorta and the ventricle, FIG. 12. If this pressure gradient has decreased sufficiently, e.g., to 30 mm Hg, the procedure is regarded as successfully completed. At this time the physician may perform another ventriculogram by injecting contrast fluid through the distal lumen of the catheter to exit the side holes 21 in the distal portion of the catheter, to observe the wall motion of the ventricle and the level of cardiac function. As the distal tip of the catheter is withdrawn from the valve into the aorta, an aortogram is performed to confirm that the valve is closing so there is no regurgitation into the ventricle during diastole. The design of the tip of the catheter also enables it to be positioned in the left main coronary artery osteum (FIG. 14). The physician can inject contrast fluid through the distal lumen into the left coronary artery to observe the coronary artery circulation. Due to the relative sizes of the distal and side holes, a sufficient volume of the contrast fluid flows into the coronary artery to allow visualization of the artery. The catheter is then removed from the femoral artery, and the artery is compressed until hemostasis occurs and the patient is returned to his room.

Figure 16:
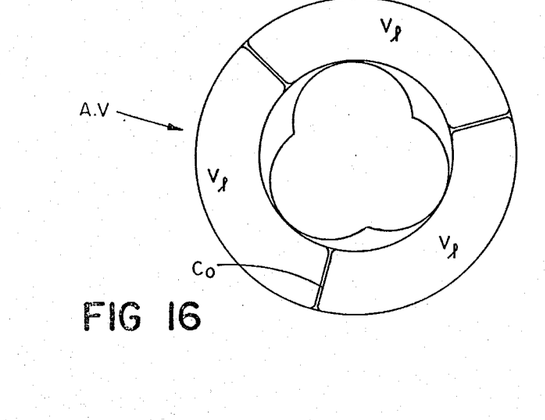
FIG. 16 is a schematic, axial view, on an enlarged scale, similar to FIGS. 4a and 9a, as viewed during the step of the procedure of FIG. 9 using an alternate embodiment of the catheter of the invention.

Other embodiments of the invention are of course possible. The balloon may have a maximum inflated diameter of up to 24 mm, selected on the basis of the patient's physical characteristics to be less than the diameter of the aortic root to avoid stretching of the root, and obstruction of flow and to avoid over distention of the leaflets that could result in regurgitation of flow or evulsion of leaflets. The balloon may have another shape, e.g., it may be a sausage shape of uniform diameter, or be specially shaped to increase blood flow through the commissures during inflation. In certain circumstances, e.g., where in addition to the leaflets having calcific plaque, the commissures of an aortic valve are fused, a multilobe balloon, e.g., formed by molding, with 3 or 4 lobes, may be employed to improve blood flow during dilatation (FIG. 16). The catheter may include a fourth lumen containing a rod, e.g., of metal or plastic, to provide additional stiffness and torqueability of the catheter over its length to the distal end of the balloon, while not affecting the soft tip. The stiffener may be fixed in the lumen, see below, or may be movable to vary the stiffened length of the catheter, and the stiffener may be tapered to vary the degree of stiffness provided.

Figure 1:
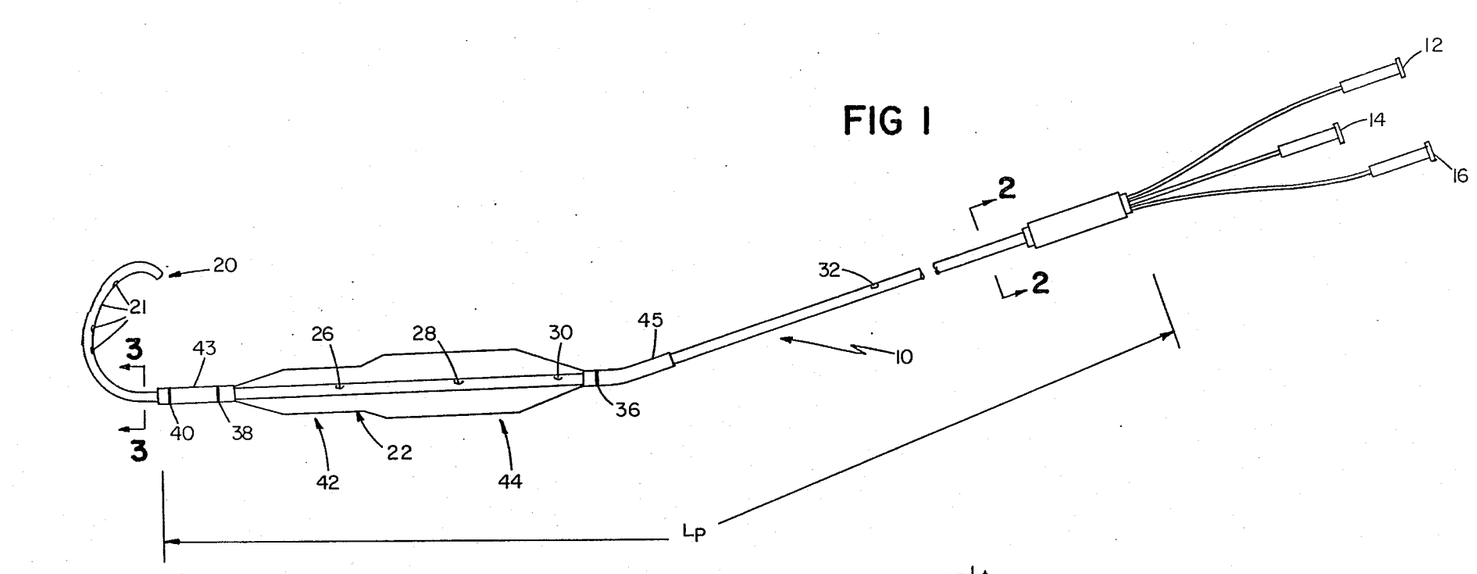
FIG. 1 is a plan view of an embodiment of the catheter of the invention.
Figure 1A:
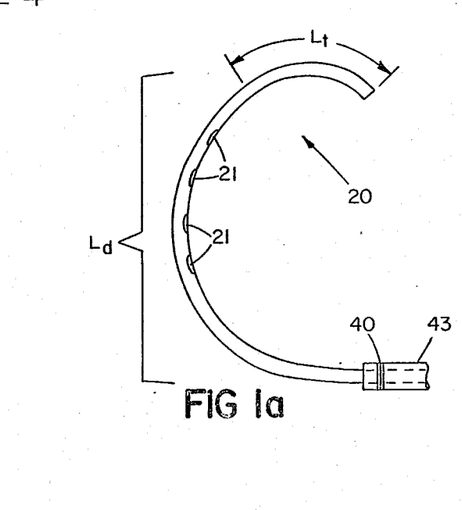
Figure 2:
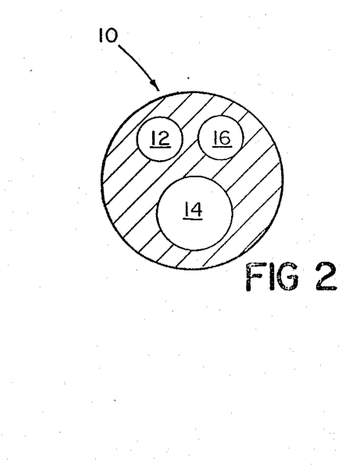
FIGS. 2 and 3 are section views taken along lines 2—2 and 3—3 of FIG. 1, respectively.
Figure 15:
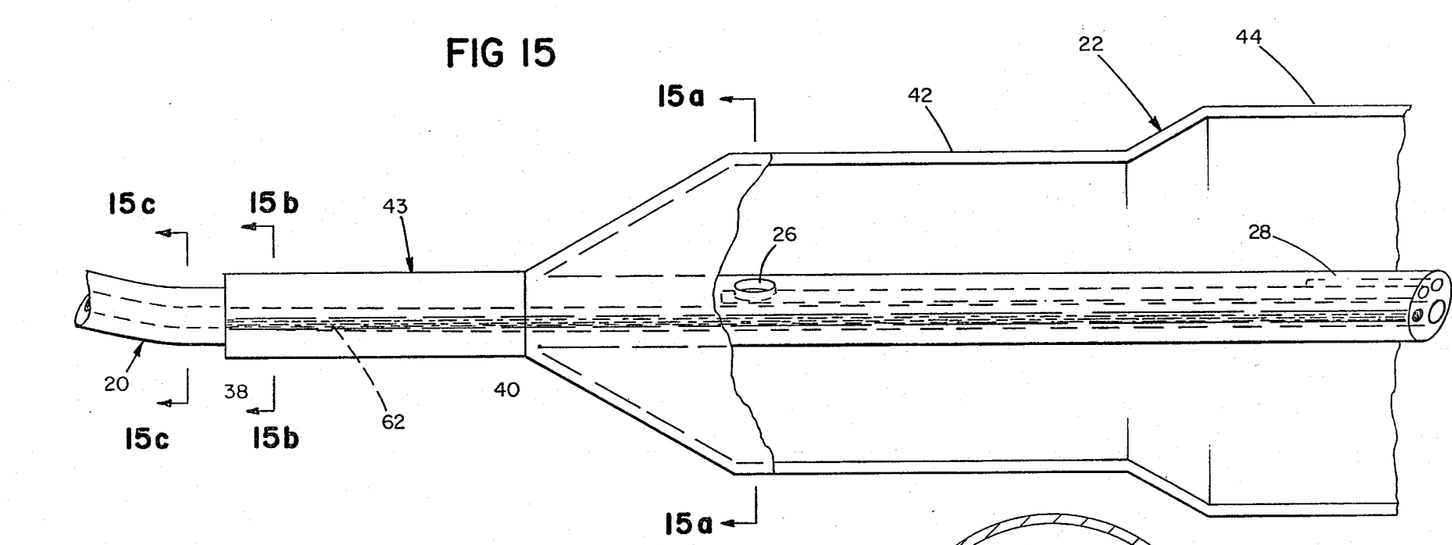
Figure 15A:
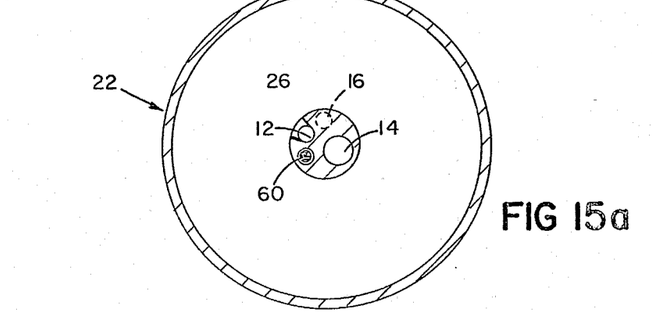
FIGS. 15a, 15b and 15c are cross-sectional views taken on corresponding lines in FIG. 15.
Figure 15B:
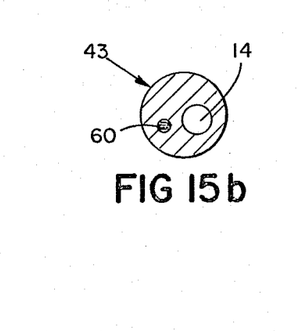
Figure 15C:
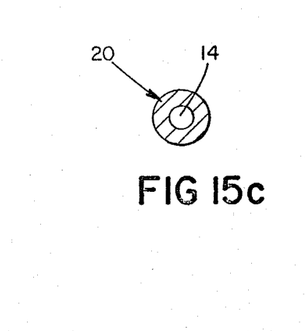

Referring to FIGS. 15-15C in another preferred embodiment, a four lumen catheter is provided, lumens 12, 14 and 16 serving the functions of the lumen of like numbers in FIG. 1, while lumen 60 is blind, i.e., it has no outlet at its distal end. A stiffener rod 60 is permanently inserted in this blind lumen and which is anchored at its distal end relative to the catheter and which is otherwise free to slide relative to the catheter e.g. during bending of the catheter or when subjected to a large change in temperature. This rod provides added stiffness in the region extending distally to the sleeve region beyond the balloon for facilitating crossing and recrossing of the stenosed aortic valve. It terminates at the end of the sleeve and thus leaves the distal portion of the catheter, $L_D$, with the designed degree of flexibility. A preferred means of fixing the distal end of the rod within the catheter is by the provision of surface roughening at 62 at the distal end, and heating the substance of the catheter, for instance during the affixation of the balloon to cause the plastic to flow into the interstices of the surface roughness, thus to provide a mechanical grip upon the roughened end of the rod.

We claim:

1. A dilatation procedure for treating patients having adult calcific aortic stenosis, in which there are calcific deposits on the leaflets of the aortic valve that impair their opening movement during systole, comprising the steps of:

introducing a dilatation balloon into the stenosed aortic valve via the aorta while the blood circulation of the patient is maintained by the heart via the aortic valve, inflating the balloon to grossly deflect the calcific leaflets of the valve in a manner avoiding blocking the outer portions of the commissures of the valve, said inflating step enabling substantial blood flow through said outer portions of the commissures during systole despite the presence in the valve of the inflated balloon, and prolonging the inflation of the balloon over an interval of at least thirty seconds spanning a large multiplicity of heart beats whereby the calcific deposits on the leaflets are disturbed to increase the pliability of the leaflets and the degree of their opening in response to systolic pressure, said calcific deposits, though thus disturbed by said dilatation, remaining as part of the leaflets so that life-threatening emboli do not form.

2. The procedure of claim 1 wherein said inflation of said balloon is so performed that, during said inflation, the calculated effective flow cross-section in said unblocked outer portions of the commissures during systole is of the order of or greater than the calculated flow cross-section during systole of the stenosed valve prior to said dilatation.

3. The procedure of claim 1 wherein said treatment is of a normally sized adult and said balloon is selected to have an average inflated diameter in the range between about 14 and 24 mm.

4. The procedure of claim 3 wherein said interval of prolonged inflation is of the order of one minute or more.

5. The procedure of claim 4 wherein said interval of prolonged inflation is no greater than about 5 minutes.

6. The procedure of claim 1 including monitoring the aortic pressure during said inflation and discontinuing said inflation upon the occurrence of substantial decrease in aortic pressure during systole.

7. The procedure of claim 1, 2, 3, 4, 5 or 6 including, prior to inflation of said balloon in said valve, measuring the pressure gradient across said aortic valve in the absence of said balloon within said valve, to establish a pre-dilatation base-line value for the flow-restriction imposed by said stenosed valve, and during said procedure, following inflation of said balloon within said valve, withdrawing said balloon from said valve and re-measuring said pressure gradient, and terminating said procedure when said gradient has substantially decreased, to about 30 mm Hg or less.

8. The procedure of claim 7 wherein, during said measurement of base-line pressure gradient value and said re-measuring of said pressure gradient, a portion of catheter extending distally from said balloon is disposed within said valve.

9. A dilatation procedure for treating patients having adult calcific aortic stenosis, including employing a catheter having an inflatable balloon, providing a multilumen dilatation catheter having at least two pressure-measuring lumens in addition to lumen means that inflates said balloon, one of said pressure-measuring lumens terminating in distal sensing port means disposed on the portion of the catheter distal of said balloon, said sensing port means adapted for measuring pressure in the left ventricle of the heart, and a second of said pressure-measuring lumens terminating in a proximal sensing port means disposed along said catheter proximal of said balloon, at least 15 cms proximal of said distal sensing port means, said second sensing port means adapted for measuring aortic pressure, said distal sensing port means being spaced distally from said balloon a distance sufficient that, while said balloon resides proximal of said aortic valve, the distal portion of the catheter extending through said valve can position said distal sensing port means entirely within the left ventricle of the heart, said procedure including the step of positioning said catheter so that said balloon lies proximal of said valve and said distal sensing port means lies entirely within the left ventricle, and while said catheter is thus disposed, by use of said distal and proximal sensing port means, measuring the pressure gradient across said valve while the heart is beating, and said procedure including the step of positioning and inflating said balloon within said valve to cause said gross deflection of said valve leaflets.

10. The dilatation procedure of claim 1 or 9 wherein a distal portion of said catheter immediately adjacent said balloon is stiffer than the distal-most portion of said catheter for remaining in said valve when said balloon is withdrawn for a pressure gradient measurement, and serving to guide said balloon for recrossing said valve, in the absence of a guidewire.

11. The procedure of claim 1 or 9 including providing a dilatation balloon catheter having a curved distal portion of a stiffness no greater than a first value over a length extending from the distal tip of the catheter to a point close to but distal of said balloon and having a second portion of substantially greater stiffness extending from said point, proximally at least beyond the portion of said catheter adapted to lie in the aortic arch during inflation of said balloon, said distal portion adapted to flex and follow a guidewire over which it is threaded to pass through said valve and into the left ventricle, and to conform atraumatically to the wall of said ventricle while the heart is beating, and said second, relatively stiffer portion of said catheter serving to resist collapse under axial compression to enable repeated thrusting of the balloon into the valve, and, by reaction of the catheter against the wall of the aortic arch, to hold the balloon in axial position within the valve during inflation while the balloon is confronted by pressurized oncoming flow of blood from the heart.

12. The procedure of claim 11 wherein said second portion of greater stiffness extends over substantially the full length of the catheter, to a region within the physician's grasp, said stiffness enabling thrusting and torquing of the catheter without disadvantageous deformation.

13. A method of aortic valvuloplasty, comprising the steps of:

A. providing an inflatable balloon catheter selected to have an effective balloon size and shape to deflelct valve leaflets without occluding the outer portions of the commissures, the balloon catheter having a relatively flexible, curved distal portion defining a conduit that has a multiplicity of side holes for measurement of pressure and injection of fluid, a relatively stiff distal segment of catheter substantially smaller than the balloon disposed between said flexible curved distal portion of catheter and said balloon, and an elongated catheter body proximal of said balloon and defining an opening proximal of said balloon for measurement of pressure;

B. advancing said balloon catheter until said distal flexible portion is passed through said valve into said ventricle, and said distal stiff segment of catheter is lodged within said valve, blood flow through the valve being only minimally impeded because of the relatively small diameter of said stiff segment;

C. measuring the pressure in the ventricle by means of said openings in said flexible distal catheter portion and measuring the pressure in the aorta by means of the proximal opening to determine the pressure gradient across the valve, such gradient being minimally affected by the presence of the small diameter, stiff segment of the catheter within the valve;

D. advancing said catheter until the balloon is positioned within said valve;

E. inflating said balloon to deflect the leaflets of the valve for treatment of adult calcific aortic stenosis;

F. deflating the balloon and withdrawing the balloon catheter until the stiff segment is again lodged within the valve;

G. repeating step C to determine the pressure gradient resulting from said treatment; and H. removing the balloon catheter from the patient.

14. The method of claim 13 including, after withdrawing the balloon as provided in step G, thrusting the balloon forward to cause said stiff segment to guide said balloon back into the valve, and thereafter repeating steps E, F and G before removing said catheter from the patient.

15. The method of claim 13 or 14 including, during the inflation of said balloon, continually monitoring the aortic pressure and deflating the balloon and withdrawing it from the valve upon the occurrence of significant drop in aortic pressure.

16. The method of claim 14 further comprising, where desirable, repeating steps E through G of claim 13 until an acceptable pressure gradient is achieved.

17. The method of claim 16 including continually monitoring aortic pressure and, under the conditions that the aortic pressure has not significantly dropped and pressure differential across the valve has remained above about 30 mm Hg, repeating steps E, F and G of claim 13.

18. The method of claim 13 or 14 wherein said balloon is of stepped construction of two different diameters, with the smaller diameter portion positioned distally of the larger diameter portion, and the method comprises dilating the valve with said smaller diameter balloon portion and then dilating the valve with said larger diameter portion.

19. The method of claim 13 or 14 further comprising the step of taking a ventriculogram by injecting a radiopaque contrast fluid through openings of said flexible distal portion while the distal portion is positioned in said ventricle and the small diameter stiff segment is lodged within said valve.

20. The method of claim 13 comprising withdrawing said distal portion of said catheter through said valve, into the aorta, injecting radiopaque contrast fluid via the distal opening of said catheter into said aorta and performing an aortogram.

21. The method of claim 13 comprising, during removal of said balloon catheter, positioning the distal end of the catheter in the left coronary artery osteum and injecting radiopaque contrast fluid via the distal opening of said catheter into said coronary artery for performing a coronary angiogram.

22. The method of claim 13 wherein said catheter is provided with a bend of between about 20° and 30° proximal of, but adjacent to, said balloon, said method comprising performing initial diagnostic catheterization of the aortic stenosis using said balloon catheter and a guidewire inserted from the aorta through said valve, over which the balloon catheter is passed, said bend facilitating the passage of said catheter over said wire, through the aorta and said valve.

23. An aortic valvuloplasty dilatation catheter having a dilatation balloon and balloon inflation lumen means, said catheter having a curved distal portion of a stiffness no greater than a first value over a length extending from the distal tip of the catheter to a point close to but distal of said balloon and having a second portion of substantially greater stiffness extending from said point, proximally at least beyond the portion of said catheter adapted to lie in the aortic arch during inflation of said balloon, said distal portion adapted to flex and follow a guidewire over which it is threaded to pass through said valve and into the left ventricle, and to conform atraumatically to the wall of said ventricle while the heart is beating, and said second, relatively stiffer portion of said catheter adapted to resist collapse under axial compression to enable repeated thrusting of the balloon into the valve, and, by reaction of the catheter against the wall of the aortic arch, to hold the balloon in axial position within the valve during inflation while the balloon is confronted by pressurized oncoming flow of blood from the heart.

24. The catheter of claim 23 wherein said second portion of greater stiffness extends over substantially the full length of the catheter, to a region within the physician's grasp, said stiffness enabling thrusting and torquing of the catheter without disadvantageous deformation.

25. The aortic valvuloplasty dilatation catheter of claim 23 wherein said first portion of said catheter incorporates a single lumen adapted to slide over a guidewire and to serve for measurement of ventricular pressure and said second portion of said catheter incorporates said lumen and at least two additional lumens, one of which is adapted for measurement of aortic pressure and another of which is adapted for inflation of said balloon.

26. The aortic valvuloplasty dilatation catheter of claim 23 in which said two portions of said catheter are integral, said first portion of said catheter being the product of heating and radial collapsing of a multiple lumen catheter of thermoplastic while only said single lumen is supported by a mandrel residing within said lumen.

27. The aortic valvuloplasty dilatation catheter of claim 23 in which a stiffener rod is permanently embedded within said catheter, said rod extending distally to said point lying distal of said balloon.

28. The aortic valvuloplasty dilatation catheter of claim 27 wherein the distal tip of said rod is fixed with respect to said catheter, proximal portions of said rod being free to slide in said lumen relative to said catheter in response for instance to bending of said catheter.

29. An aortic valvuloplasty dilatation catheter comprising
a multilumen catheter having a dilatation balloon, balloon inflation lumen means, at least two pressure-measuring lumens, and means for repeatedly introducing said diltation balloon into an aortic valve for treatment of adult calcific aortic stenosis and for withdrawing the balloon proximally from the valve for measuring pressure in the heart and in the aorta for determination of aortic valve efficiency, said means for introducing comprising a flexible distal tip portion adapted to be introduced through the aortic valve, into the left ventricle of the heart, and an extended sleeve proximal of said distal tip portion and integral with said balloon, said sleeve extending distally of said balloon a distance between about 1 and 2 centimeters and, serving to stiffen the corresponding portion of the catheter, said sleeve having a diameter sufficiently small so as not to impede blood flow through the valve,
one of said pressure-measuring lumens terminating in a distal sensing port means disposed on said distal tip portion of the catheter, distal of said balloon, said sensing port means adapted for measuring pressure in the left ventricle of the heart,
a second of said pressure-measuring lumens terminating in a proximal sensing port means disposed along said catheter proximally of said balloon, said second sensing port means adapted for measuring aortic pressure, said distal sensing port means being spaced distally from said balloon a distance sufficient that, while said balloon resides proximal of the aortic valve, the distal tip portion of the catheter extending through the aortic valve can position said distal sensing port means entirely within the left ventricle of the heart,
whereby when said catheter is positioned so that said balloon lies proximally of the aortic valve while said distal sensing port means lies entirely within the left ventricle, by use of said distal and proximal sensing port means, the pressure gradient across the valve can be measured while the heart is beating,
and whereby, by relatively little motion from said position, said balloon can be positioned within the valve to be inflated to cause gross deflection of the leaflets of the valve for treatment of adult calcific aortic stenosis.

30. The aortic vavuloplasty dilatation catheter of claim 23, 24, 25, 26, 27, 28 or 29 wherein said balloon is of stepped construction of two different diameters and having tapered transition portions, the smaller diameter portion of said balloon comprising the distal portion of the balloon being between about 2 and 2.5 cm in length and having a diameter of between about 14 and 18 mm and the larger diameter portion of said ballon comprising the proximal portion of the balloon and being between about 3 and 3.5 cm in length and having a diameter between of about 18 and 24 mm.

31. The catheter of claim 30 wherein said tapered transition portions at the ends of said balloon have a length between about one-half and one cm and the transition between the two balloon diameters having a length of the order of one-half cm.

32. The aortic valvuloplasty dilatation catheter of claim 23, 24, 25, 26, 27, 28 or 29 having a bend of between about 20° and 30° located immediately proximal of said balloon and adapted to ease the passage of the catheter through the aortic arch.

33. The aortic valvuloplasty catheter of claim 23, 24, 25, 26, 27, 28 or 29 having a distal portion of compound curvature, the distal-most portion having a smaller radius of curvature than the portion lying proximal thereof.

34. The catheter of claim 33 wherein the total arc of said curvature is between about 200° and 250°, and said catheter is adapted, when the distal tip is withdrawn into the aorta from said valve, to assume a position within the osteum of a coronary artery to enable injection of radiopaque contrast fluid therein, whereby an angiogram of the coronary artery can be obtained.

35. The catheter of claim 33 having a distribution of side holes along the length of the distal portion, on the inside of the curve, the proximal-most hole being at least about 3 cms distal of the end of said balloon, for the purpose of left ventricular angiography before the valvuloplasty procedure and supravalvular aortograms.

36. The catheter of claim 34 wherein each said side hole has a flow cross-sectional area between about 1.5 and 2.0 m$^2$.

37. The catheter of claim 35 wherein there is provided a further hole at the end of said distal poriton, said further hole having a flow cross-sectional area substantially greater than that of any of said side holes.

38. The aortic valvuloplasty dilatation catheter of claim 23, 24, 25, 26, 27, 28 or 29 wherein said balloon is cylindrical and has a diameter between about 14 and 24 mm and is about 3½ to 4½ cm in length.

39. The aortic valvuloplasty dilatation catheter of claim 23, 24, 25, 26, 27, 28 or 29 wherein said balloon is of noncircular cross-section, having a multiplicity of lobes for the purpose of enhancing blood flow past said balloon.

40. The aortic valvuloplasty dilatation catheter of claim 23, 24, 25, 26, 27, 28 or 29 further comprising a pair of spaced-apart radiopaque indicators positioned on the catheter distal of said balloon to enable the physician to accurately determine the position of said portion of said catheter relative to the valve when said balloon is withdrawn from the valve, with one of said markers lying on each side of the valve.

* * * * *

UNITED STATES PATENT AND TRADEMARK OFFICE
CERTIFICATE OF CORRECTION

PATENT NO. : 4,777,951

DATED : October 18, 1988

INVENTOR(S) : Alain Cribier, et al.

It is certified that error appears in the above-identified patent and that said Letters Patent is hereby corrected as shown below:

Under Other Publications:

"Aortenk-lappe" should be --Aorten-klappe--;

Lababidi, Z. et al., "Percutaneos" should be --Percutaneous--;

Inoue, "K," should be --K.--;

Col. 1, line 57, "balldon" should be --balloon--;

Col. 2, lines 24-43, "Summary of the Invention" should read "Summary of Our Development" and should be centered; "In the beginning" starts a new paragraph, and the remainder should extend between the margins;

Col. 7, line 10, "physical" (second occurrence) should be --Physical--;

Col. 8, line 65, "aoriic" should be --aortic--;

Col. 9, line 35, "0.46 cm" should be --0.46 $cm^2$--;

Col. 17, line 2, "deflelct" should be --deflect--;

Col. 20, line 41, "poriton" should be --portion--.

Signed and Sealed this

Thirtieth Day of May, 1989

*Attest:*

DONALD J. QUIGG

*Attesting Officer*   *Commissioner of Patents and Trademarks*